(12) United States Patent
Lv et al.

(10) Patent No.: US 9,115,150 B2
(45) Date of Patent: Aug. 25, 2015

(54) CAMPTOTHECIN COMPOUND CONTAINING STABLE 7-MEMBERED LACTONE RING, PREPARATION METHOD AND USE

(75) Inventors: Wei Lv, Shanghai (CN); Shanbao Yu, Shanghai (CN); Yu Luo, Shanghai (CN); Yi Chen, Shanghai (CN); Jian Ding, Shanghai (CN)

(73) Assignees: EAST CHINA NORMAL UNIVERSITY, Shanghai (CN); SHANGHAI INSTITUTE OF MATERIA MEDICA, CHINESE ACADEMY OF SCIENCES, Shanghai (CN); NANJING LUYESIKE PHARMACEUTICAL CO., LTD., Nanjing (CN)

( * ) Notice: Subject to any disclaimer, the term of this patent is extended or adjusted under 35 U.S.C. 154(b) by 0 days.

(21) Appl. No.: 14/112,583

(22) PCT Filed: Apr. 13, 2012

(86) PCT No.: PCT/CN2012/073983
§ 371 (c)(1),
(2), (4) Date: Jan. 6, 2014

(87) PCT Pub. No.: WO2012/142926
PCT Pub. Date: Oct. 26, 2012

(65) Prior Publication Data
US 2014/0128421 A1     May 8, 2014

(51) Int. Cl.
*C07D 491/22* (2006.01)
(52) U.S. Cl.
CPC ............................. *C07D 491/22* (2013.01)
(58) Field of Classification Search
CPC .................................................. C07D 491/22
USPC ........................................ 514/283, 279; 546/48
See application file for complete search history.

(56) References Cited

U.S. PATENT DOCUMENTS

| | | | |
|---|---|---|---|
| 5,981,542 A | 11/1999 | Bigg et al. | |
| 6,723,853 B2 * | 4/2004 | Curran et al. | 546/294 |
| 6,762,301 B2 * | 7/2004 | Bigg et al. | 546/48 |
| 6,933,302 B2 * | 8/2005 | Yang | 514/283 |

OTHER PUBLICATIONS

International Search Report for PCT/CN2012/073983, mailed Jul. 19, 2012.
Lavergne et al., "Topoisomerase I-Mediated Antiproliferative Activity of Enantiomerically Pure Fluorinated Homocamptothecins," J. Med. Chem., vol. 43, Published on Web May 10, 2000, pp. 2285-2289.
Lavergne et al., "Homocamptothecins: E-Ring Modified CPT Analogues," Annals New York Academy of Sciences, 2000, pp. 100-111.

* cited by examiner

*Primary Examiner* — Rita Desai
(74) *Attorney, Agent, or Firm* — Nixon & Vanderhye P.C.

(57) ABSTRACT

Provided are a camptothecin compound containing 7-membered lactone ring, as shown in general formula I, and pharmaceutically acceptable salt thereof, as well as the preparation method and use thereof. In general formula I, $R_1$ is H, a C1~C3 alkyl, acetyl or propionyl; $R_2$ is H, a C1~C6 alkyl, a C3~C6 cycloalkyl, piperidyl; or a C1~C6 alkyl substituted by an amino; $R_3$ is H, a C1~C3 alkyl, or a C1~C6 alkyl substituted by an amino; $R_4$ is H, a hydroxyl, or a C1~C6 alkoxy; $R_5$ is H, or a C1~C6 alkoxyl; or $R_4$ and $R_5$ are linked to each other to form —$OCH_2O$— or —$OCH_2CH_2O$—. The compound has good anti-tumor activity, and can be clinically used via oral administration, intravenous injection, and intramuscular injection, among others.

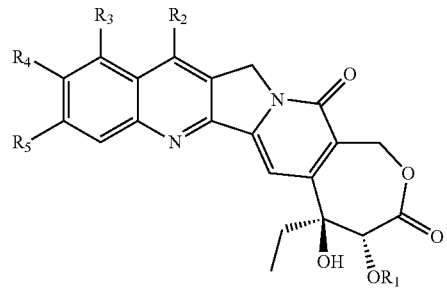

8 Claims, No Drawings

CAMPTOTHECIN COMPOUND CONTAINING STABLE 7-MEMBERED LACTONE RING, PREPARATION METHOD AND USE

This application is the U.S. national phase of International Application No. PCT/CN2012/073983, filed 13 Apr. 2012, which designated the U.S. and claims priority to China Application No. 201110097364.2, filed 18 Apr. 2011, the entire contents of each of which are hereby incorporated by reference.

TECHNICAL FIELD

The present invention relates to a novel camptothecin compound with improved anti-tumor activity, the method for preparing the same and the use thereof. More specially, the present invention relates to a novel camptothecin derivative with the following formula (I), the preparation method thereof, and the use of the compound in the field of anti-tumor.

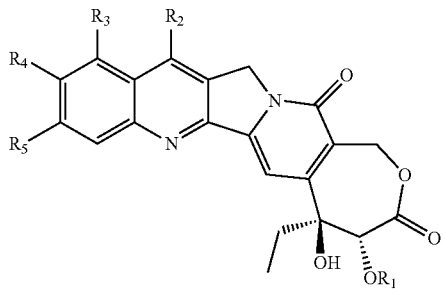

I

TECHNICAL BACKGROUND

Camptothecin (CPT) is an alkaloid which was extracted and isolated from *camptotheca acuminate*, a Chinese unique plant, by Wall, a US scientist, in 1966, and has remarkable activities against rat leukaemia L1210 system. Camptothecin is an alkaloid having a pyridone structure in its structure, and has a particular structure as follows, Compound 1:

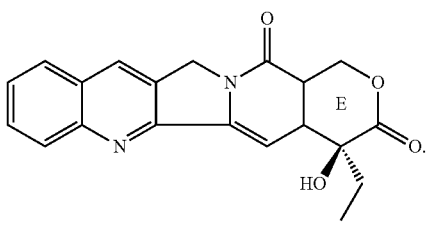

(1)

In the structure, there is a pentacyclic structure, and Ring E is a 6-membered lactone ring containing an alpha-hydroxyl group in S-type absolute configuration. Camptothecin is of interesting due to its good activities against leukemia L1210, since it was extracted and isolated for the first time.

Thereafter, a series of camptothecin derivatives have gradually become new anticancer drugs that are already available in the market or in various development stages, for their unique bioactive mechanisms and good medicinal property, for example, 10-hydroxylcamptothecin (compound 2) widely applied in clinical therapy in China; 10-hydroxyl-9-dimethylaminomethylcamptothecin (compound 3, Topotecan) marked in 1996 and used as a second-line drug for treating ovarian cancer; compound 4 (SN-38) with excellent anti-tumor activity, and its water soluble prodrug, Irinotecan (compound 5) marked in 1994 and used for treating colorectal cancer; Belotecan (compound 6) approved for marketing in Korea in 2005 and used for treating prostatic cancer.

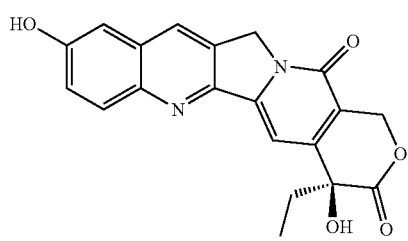

2

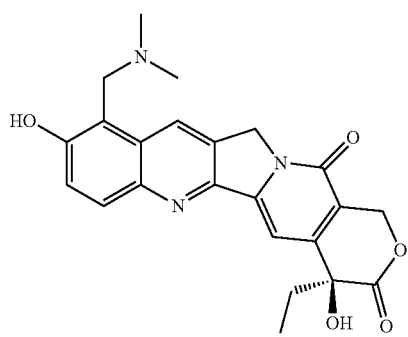

3

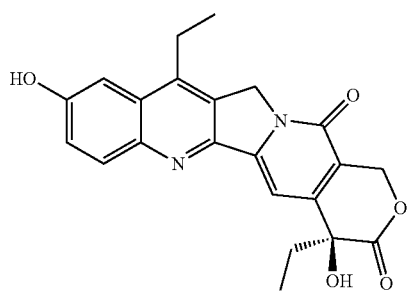

4

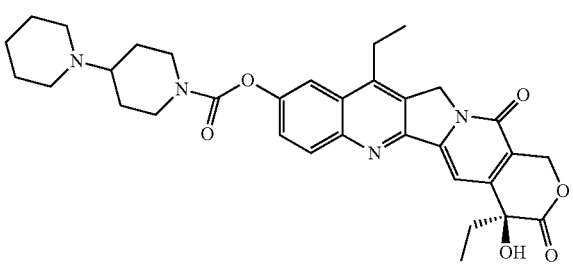

5

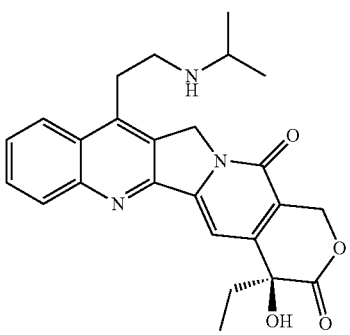

6

In addition, many other camptothecin derivatives are in various clinical trial stages. However, the current results indicate that these compounds have less curative effect than Topotecan or Irinotecan. Therefore, there is a need for camptothecin derivatives with better curative effect.

The existing camptothecin derivatives have drawbacks that lactone ring is unstable and may be opened to form an inactive structure under physiological conditions, which results in severe problems such as lowered curative effect and increased toxicity, as indicated as follows:

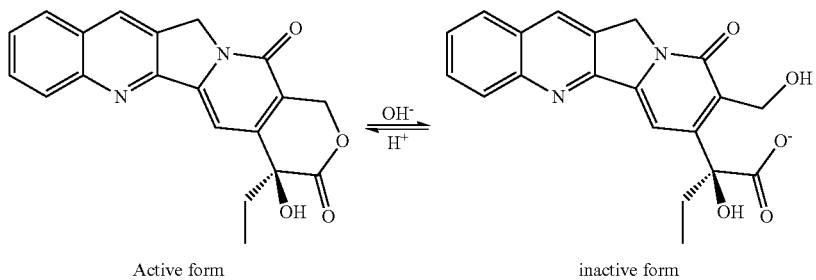

Active form          inactive form

In order to solve this problem, homocamptothecin was suggested. The obtained compound 7 (Diflomotecan) has excellent anti-tumor activity and enter the phase III of clinical study. However, the clinical trial failed since the lactone ring thereof opened under physiological conditions could not be closed again under the same condition, as shown in the following reaction scheme:

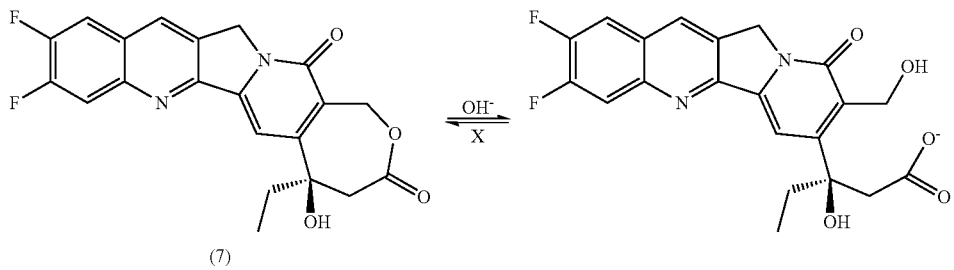

(7)

Thus, it still needs novel camptothecin compounds with stable lactone ring.

DISCLOSURE OF THE INVENTION

One object of the present invention is to provide a novel camptothecin compound with 7-membered lactone ring and pharmaceutically acceptable salts thereof, which is characterized in its stable lactone ring, and thus has advantages such as less side effect and high activity.

Another object of the present invention is to provide a method for preparing the said novel camptothecin compound and pharmaceutically acceptable salts thereof.

Yet another object of the present invention is to provide a composition for treating cancer, comprising a therapeutically effective amount of one or more selected from the group consisting of the novel camptothecin compound and pharmaceutically acceptable salts thereof, and pharmaceutically acceptable carriers. The said pharmaceutically acceptable salts include, but not limit to, addition salts of the said compound with hydrochloric acid, sulphuric acid, phosphoric acid, methane sulfonic acid, succinic acid, maleic acid, fumaric acid, tartaric acid, citric acid and so on.

Yet another object of the present invention is to provide the use of the said camptothecin compound and pharmaceutically acceptable salts thereof in preparing a medicament for anti-tumor. More specially, the present invention provides the use of the said camptothecin compound and pharmaceutically acceptable salts thereof in preparing a medicament for treating colon or lung cancer.

The acidity of the carboxyl group can be enhanced by introducing an electron-withdrawing group into alpha position of the carboxyl group according to the organic knowledge. In the present invention, a group such as hydroxyl, alkoxyl, ester group etc. is introduced onto the position 20a of homocamptothecin. As a result, such kind of compounds are found that they have enhanced stability of lactone ring and good anticancer activity.

The present invention relates to a novel camptothecin derivative formed by introducing a hydroxyl, alkoxyl, or ester group onto position 20a of a homocamptothecin derivative. They have enhanced anticancer activity.

The camptothecin compound with 7-membered lactone ring, and pharmaceutically acceptable salts thereof have a structure represented by following formula (I):

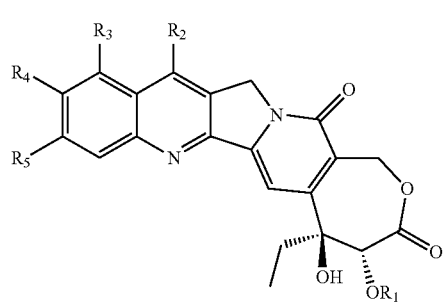

I wherein,

R₁ is H, C1~C3 alkyl, acetyl or propionyl; preferably, R₁ is H or acetyl;

R₂ is H, C1~C6 alkyl, C3~C6 cycloalkyl, piperidyl, or C1~C6 alkyl substituted by amino; preferably, R₂ is H or C1~C3 alkyl; more preferably, R₂ is H or ethyl;

R₃ is H, C1~C3 alkyl, or C1~C6 alkyl substituted by amino; preferably, R₃ is H or C1~C3 alkyl;

R₄ is H, hydroxyl, or C1~C6 alkoxyl; preferably, R₄ is H, hydroxy, or C1~C3 alkoxyl; more preferably, R₄ is H, hydroxyl, or methoxy;

R₅ is H, or C1~C6 alkoxyl; preferably, R₅ is H or C1~C3 alkoxyl; more preferably, R₅ is H;

Or, R4 and R5 are linked to each other to form —OCH₂O— or —OCH₂CH₂O—.

Preferably, the said camptothecin compound with 7-membered lactone ring, and pharmaceutically acceptable salts thereof are:

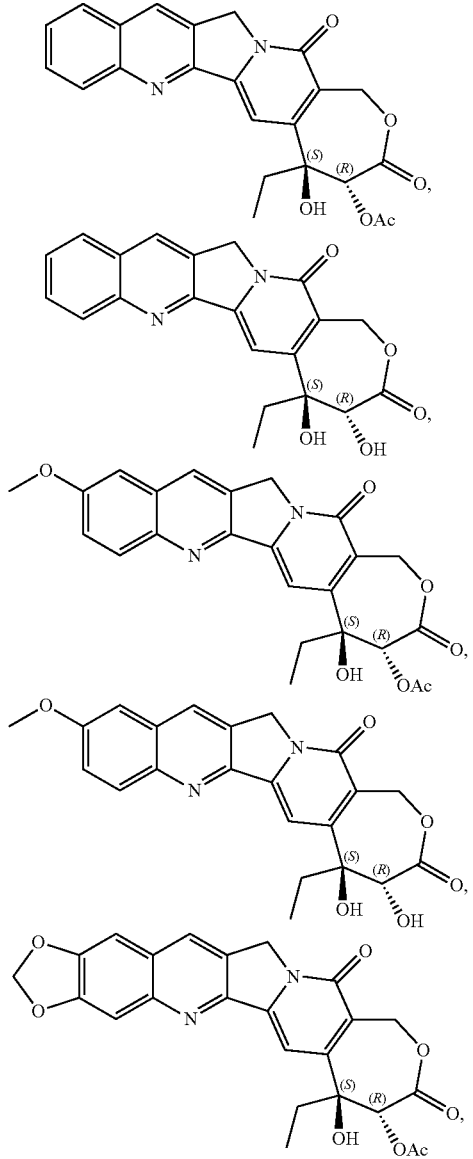

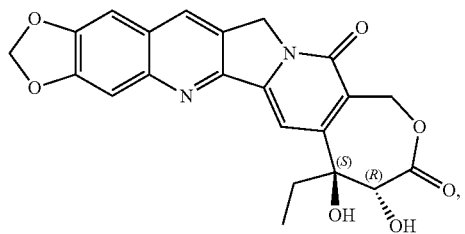

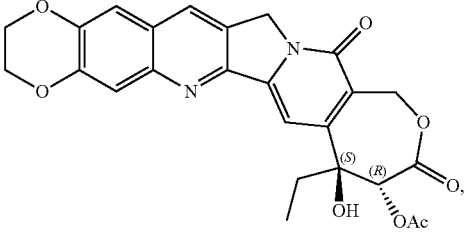

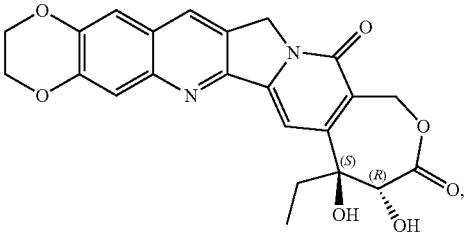

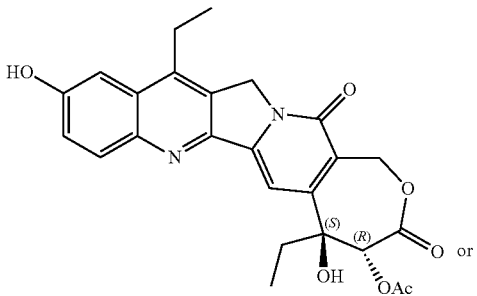

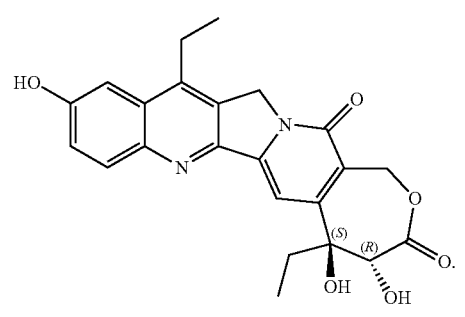

The present invention provides a method for preparing the said camptothecin compound with 7-membered lactone ring, and pharmaceutically acceptable salts thereof, comprising the following steps:

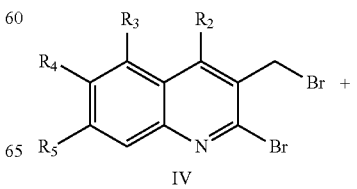

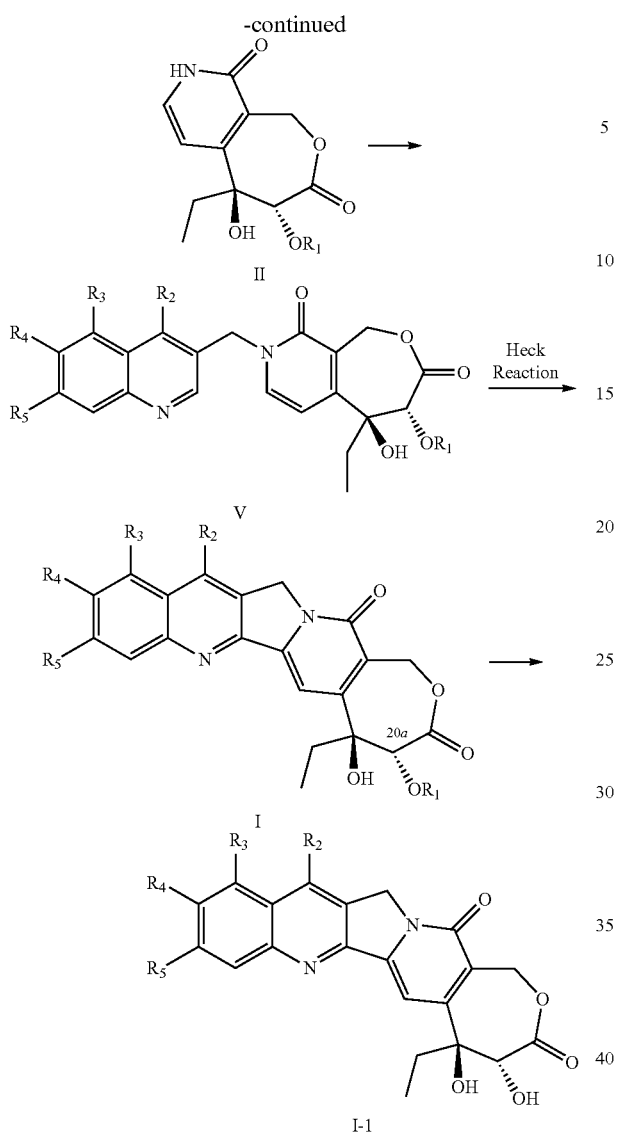
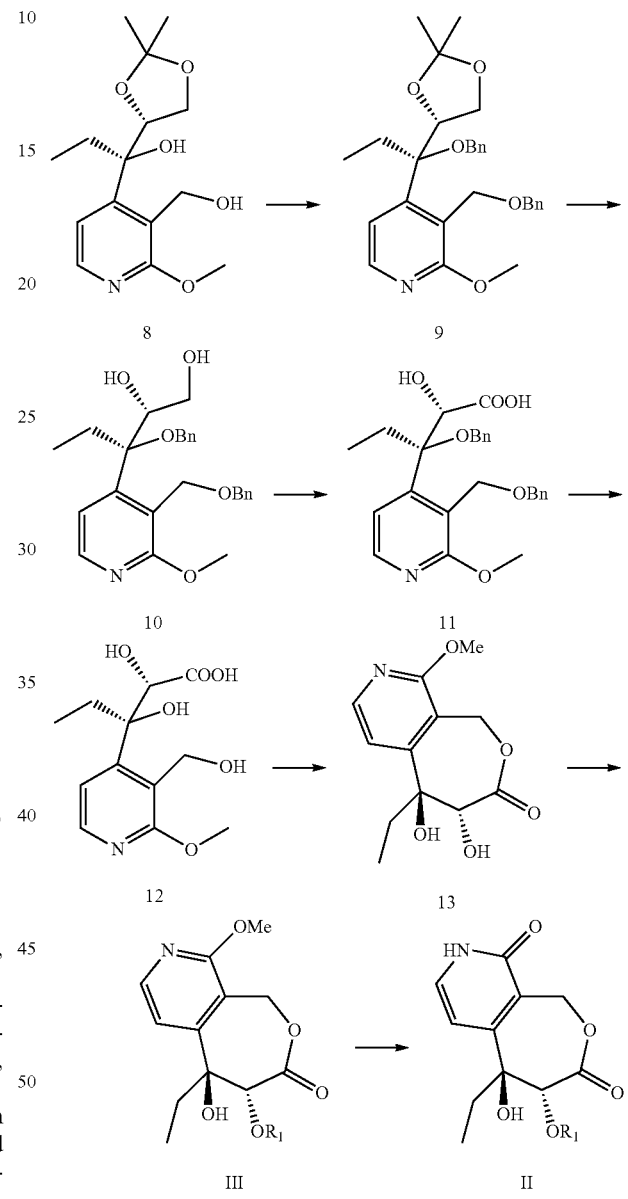

wherein, R1, R2, R3, R4 and R5 are defined as above, provided that R1 is not H.

Among others, the compound of formula IV may be prepared according to the method reported in the following literatures: 1), *The Journal of Organic Chemistry* 2000, 65, 5212; 2) *Tetrahedron* 1997, 53, 10953.

i) Compound II performs a N-alkylation reaction with compound IV in the presence of an alkali to obtain compound V. The alkali may be potassium tert-butoxide, sodium tert-butoxide or sodium hydride, etc., preferably potassium tert-butoxide. The reaction solvent may be tetrahydrofuran, dimethyl formamide or ethylene glycol dimethyl ether, etc, preferably ethylene glycol dimethyl ether.

ii) Compound V is subjected to Heck reaction in the presence of a palladium catalyst to prepare the compound represented by formula I. Among others, the palladium catalyst may be palladium acetate or palladium chloride, preferably palladium acetate. The phosphorus ligand needed by the reaction may be triphenyl phosphine, tri-(o-tolyl)phosphine, tri (tert-butyl)phosphine or tricyclohexyl phosphine. The alkali used in the reaction may be potassium carbonate, potassium acetate or sodium carbonate etc., preferably, potassium carbonate. The reaction solvent may be acetonitrile, dimethyl formamide or toluene, preferably acetonitrile.

iii) Optionally, the compound represent by formula I may be hydrolyzed to obtain compound I-1 in the case of that R1 is acetyl.

The intermediate compound II may be prepared by the following method:

wherein, R1 is defined as above, provided that R1 is not H.

The starting material compound 8 may be prepared according to Chinese patent application 200910054400.X, which is filed by the present applicant.

1) Compound 8 performs an etherification with benzyl bromide or benzyl chloride in the presence of an alkali to form compound 9. The reaction solvent may be tetrahydrofuran, toluene or N,N-dimethyl formamide, etc. The alkali employed in the reaction may be an inorganic alkali or an organic alkali, such as sodium hydride, sodium hydroxide, potassium carbonate, triethanol amine or diethyl isopropyl amine, preferably sodium hydride. The reaction temperature may be a temperature from 0 to 100° C., preferably room temperature.

2) Compound 9 is hydrolyzed in the present of an acid to form compound 10. The acid employed in this step may be a diluted hydrochloric acid with a concentration from 1N to 12N or a diluted sulphuric acid with a concentration from 10 wt % to 45 wt %. The solvent employed in this step may be methanol, ethanol, isopropanol, or tetrahydrofuran, preferably methanol. The reaction temperature of this step may be a temperature from 20 to 60° C.

3) Compound 10 is oxidized in the presence of an oxidant to produce compound 11. The oxidant employed in this step may be (i) sodium hypochlorite, sodium chlorite and 2,2,6,6-tetramethyl-piperidin-1-oxyl(TEMPO); or (ii) sodium hypochlorite, sodium chlorite and N-methylmorpholine-N-oxide (NMO), and the oxidation system (i) is preferable. The solvent employed in this step may be a saturated solution of potassium dihydrogen phosphate in tetrahydrofuran, a saturated solution of potassium dihydrogen phosphate in tert-butanol, or a saturated solution of potassium dihydrogen phosphate in acetonitrile, preferably the saturated solution of potassium dihydrogen phosphate in tetrahydrofuran. The reaction temperature of this step may be a temperature from 20 to 55° C.

4) Compound 11 is deprotected by removing the protection group of benzyl in the presence of a catalytic hydrogenation system to obtain compound 12. The catalytic system employed in this step is Pd/C or $PtO_2$ to perform hydrogenation and remove the protection group, and preferably, Pd/C is employed as the metallic catalyst. The solvent may be methanol or ethanol. The reaction temperature is a temperature from 20 to 60° C.;

5) Compound 12 is converted into compound 13 containing a lactone ring in the presence of an acid. The acid employed in this step may be trifluoroacetic acid. The solvent used in this step may be anhydrous tetrahydrofuran, anhydrous dichloromethane, anhydrous methanol, or anhydrous ethanol, preferably methanol. The reaction temperature in this step is a temperature from 0 to 40° C.

6) In the case of that R1 is C1-C3 alkyl, compound 13 undergoes an etherification reaction with a chlorinated or brominated C1-C3 alkane in the presence of an alkali to obtain compound III. The alkali employed in the etherification reaction may be sodium hydride. The reaction solvent may be tetrahydrofuran or N,N-dimethyl formamide, and the like.

In the case of that R1 is acetyl or propionyl, compound 13 is acylated by an anhydride or acyl chloride corresponding to the product in the presence of an alkali to form compound III. Among others, the corresponding anhydride or acyl chloride employed in the acylation reaction may be acetic anhydride, propionic anhydride, acetyl chloride or propionyl chloride. The alkali employed in this step may be an organic alkali or an inorganic alkali, wherein the organic alkali may be triethylamine, diisopropylethylamine or pyridine, and the inorganic alkali may be one or more selected from the group consisting of alkali metal hydroxides and alkaline earth metal hydroxides, for example, one or more selected from the group consisting of carbonates and bicarbonates. Preferably, the organic alkali is used as the reactant.

7) In the case of that $R_1$ is acetyl, or propionyl, compound III is demethylated in the presence of iodotrimethylsilane, boron tribromide, or silicon tetrachloride, preferably iodotrimethylsilane, to obtain a 2-pyridinone compound of key intermediate II. The reaction solvent may be acetonitrile, or dichloromethane; preferably acetonitrile. The reaction temperature in this step is a temperature from 20 to 50° C.

In the case of that $R_1$ is C1~C3 alkyl, compound III is demethylated in the presence of a hydrochloric acid (1-12N) to obtain the intermediate II.

The compound provided by the present invention has good anti-tumor activity, and can be clinically administered orally, intravenously, intramuscularly, and the like.

BEST MODE FOR CARRYING OUT THE INVENTION

The novel camptothecin derivative and the preparation thereof are described in more detail in the following examples, but these examples should not be construed as limiting the present invention.

EXAMPLE 1

Preparation of 4-{[(1S)-1-benzyloxyl]-1-[(4R)-2,2-dimethyl-[1,3]dioxolan-4-yl]-propyl}-3-benzyloxy-2-methoxy-pyridine (Compound 9)

2.0 g of compound 8 and 0.5 g of sodium hydride in 60 ml of anhydrous TFT were reacted at room temperature for a while under nitrogen, followed by addition of 1.5 ml of benzyl bromide. After refluxing for 1 h under heating, the reaction was stopped, and the reaction mixture was cooled to room temperature. Then a saturated ammonium chloride aqueous solution was added to quench the reaction. The obtained mixture was extracted with ethyl acetate, and the organic phase was combined and washed with water and saturated sodium chloride aqueous solution, dried over anhydrous sodium sulfate, and filtrated. The obtained filtrate was rotary evaporated to obtain a crude product, which was subjected to silica gel column chromatography to obtain 2.8 g of colorless liquid. Yield: 87.5%.

$^1$HNMR ($CDCl_3$) (ppm): 0.87 (3H, t), 1.35 (6H, s), 2.20 (1H, m), 2.31 (1H, m), 3.87 (1H, t), 3.96 (3H, s), 3.99 (1H, t), 4.45 (2H, s), 4.88 (1H, d), 4.68 (2H, t), 4.80 (1H, t), 4.88 (1H, d), 7.12 (1H, d), 7.12-7.34 (10H, m), 8.10 (1H, d).

EXAMPLE 2

Preparation of (2R,3S)-3-benzyloxy-3-(3-benzyl-methoxy-2-methoxy-pyridin-4-yl)-pentane-1,2-diol (Compound 10)

The compound 9 was dissolved in 50 ml of methanol at room temperature, followed by dropwise addition of 6 ml of 3N hydrochloric acid. After the reaction was continued for a while at room temperature, the reaction was stopped. The reaction mixture was subjected to rotary evaporation to remove methanol, and then extracted with ethyl acetate. The ethyl acetate phase was combined, washed with water and saturated saline aqueous solution, dried over anhydrous sodium sulphate, filtered, and rotarily evaporated to obtain 2.1 g of thick solid with a yield of 92.1%.

$^1$HNMR ($CDCl_3$) (ppm): 0.90 (3H, t), 2.16 (1H, m), 2.30 (1H, s, br), 2.45 (1H, m), 3.31 (1H, m), 3.54 (1H, m), 3.93 (3H, s), 3.99 (1H, s, br), 4.11 (1H, m), 4.35 (1H, d), 4.44 (1H, d), 4.53 (1H, d), 4.67 (1H, d), 4.74 (1H, d), 4.96 (1H, d), 6.88 (1H, d), 7.26-7.42 (10H, m), 8.09 (1H, d).

EXAMPLE 3

Preparation of (2S,3S)-3-benzyloxy-3-(3-benzyloxymethyl-2-methoxy-pyridin-4-yl)-2-hydoxy-pentanoic acid (Compound-11)

The compound 10 (13.37 g) was dissolved in 65 ml of saturated potassium dihydrogen phosphate solution in acetonitrile, followed by addition of 5.6 g of sodium chlorite, 1.3 g of 2,2,6,6-tetramethyl-piperidin-1-oxyl, and 2.6 ml of sodium hypochlorite aqueous solution at room temperature. After the reaction was conducted for 3-4 h, 120 ml of water was added. The mixture was extracted with dichloromethane, and the organic phase was combined, washed with water and saturated saline aqueous solution, dried over anhydrous sodium sulphate, filtered, and rotarily evaporated to obtain 12.1 g of crude product, which was used for the next step without purification. Yield: 98.5%.

$^1$HNMR (CDCl$_3$) (ppm): 0.88 (3H, t), 2.42 (1H, m), 2.63 (1H, s), 3.93 (3H, s), 4.20 (2H, m), 4.55 (3H, m), 4.77 (1H, d), 4.92 (1H, d), 6.88 (1H, d), 7.26-7.42 (10H, m), 8.09 (1H, d).

EXAMPLE 4

Preparation of (2S,3S)-2,3-dihydroxyl-3-(3-hydroxymethyl-2-methoxy-pyridin-4-yl)-pentanoic acid (Compound 12)

The product (12.2 g) obtained in above step was dissolved in 120 ml of absolute methanol. 1.3 g of Pd/C (10%) was added to conduct hydrogenation for 12 h at room temperature under normal pressure. The reaction mixture was filtered, and the resulted filter cake was washed with methanol for two or three times. The solution was combined and rotarily evaporated to obtain 6.6 g of crude product with a yield of 90%, which was used for the next step without purification.

$^1$HNMR (CDCl$_3$) (ppm): 0.88 (3H, t), 1.85 (2H, m), 2.32 (1H, s), 2.42 (1H, s), 2.63 (1H, s), 3.93 (3H, s), 4.66 (1H, m), 4.80 (2H, s), 6.72 (1H, d), 7.98 (1H, d).

EXAMPLE 5

Preparation of (5S,6R)-5-ethyl-5,6-dihydroxyl-1-methoxy-5,9-dihydro-6H-8-oxa-2-aza-benzocycloheptene-7-one (Compound 13)

The product (6.6 g) obtained in above step was dissolved in 100 ml methanol. 4 ml of trifluoroacetic acid was added thereto, and the reaction was conducted for 24 h at room temperature. The reaction mixture was rotarily evaporated to obtain 6.5 g of crude product, which was used for the next step without purification.

EXAMPLE 6

Preparation of (5S,6R)-5-ethyl-5-hydroxyl-1-methoxy-7-oxa-5,6,7,9-tetrahydro-8-oxa-2-aza-benzocycloheptene-6-yl acetate (Structure Formula III, R$_1$=CH$_3$CO—)

The compound 13 (8.5 g), 4-dimethylaminopyridine (0.82 g), triethylamine (8.4 ml) were dissolved in 100 ml anhydrous methylene chloride, and cooled to 0° C. under ice water. Acetylchloride (4.4 ml) was added dropwisely to the system. After that, the system was placed at room temperature to react for 2 h. Then, 50 ml of saturated ammonium chloride aqueous solution was added. The mixture was separated, and the water layer was extracted with dichloromethane for 2 or 3 times. The dichloromethane phase was combined, washed with water and saturated saline aqueous solution, dried over anhydrous sodium sulfate, filtered, and rotarily evaporated to obtain 10 g of crude product, which was subjected to silica gel column chromatography (petroleum ether:ethyl acetate=2:1) to obtain 4.5 g of white solid. Yield: 53%.

$^1$HNMR (CDCl$_3$) (ppm): 0.88 (3H, t), 2.08 (1H, m), 2.18 (1H, m), 2.29 (3H, s), 2.91 (1H, s), 3.98 (3H, s), 5.23 (2H, d), 5.74 (2H, d), 7.20 (1H, d), 8.20 (1H, d).

EXAMPLE 7

Preparation of (5S,6R)-5-ethyl-5-hydroxyl-1,7-dioxa-1,2,5,6,7,9-hexahydro-8-oxa-2-aza-benzocyclohepten-6-yl acetate (structure Formula II, R$_1$=CH$_3$CO—)

The compound (4.5 g) obtained in example 6 was dissolved in 100 ml of anhydrous acetonitrile, and 4.6 g of sodium iodide was added thereto. 3.9 ml of chlorotrimethylsilane was added dropwisely therein to form trimethylsilyl iodide on site. After the addition, the mixture was allowed to react for 4 h, and poured into 100 ml of water. The mixture was extracted with dichloromethane for 4 to 5 times, and the organic phase was combined, washed with saturated saline aqueous solution, dried over anhydrous sodium sulfate, filtered and rotarily evaporated to obtain a light yellow solid, which was subjected to silica gel column chromatography (dichloromethane:methanol=50:1) to obtain 2.1 g of white solid. Yield: 52%.

$^1$HNMR (DMSO-D$^6$) (ppm): 0.63 (3H, t), 1.81 (1H, m), 2.08 (1H, m), 2.19 (3H, s), 5.30 (1H, d), 5.50 (1H, d), 5.88 (1H, s), 6.01 (1H, s), 6.37 (1H, d), 7.39 (1H, d), 11.81 (1H, s).

EXAMPLE 8

Preparation of (20S,20aR)-20a-acetoxyhomocamptothecin (Compound ysb-1)

Preparation of (5S,6R)-2-(2-bromine-quinolin-3-yl methyl)-5-ethyl-5-hydroxyl-1,7-dioxa-1,2,5,6,7,9-hexahydro-8-oxa-2-aza-benzocyclohepten-6-yl acetate 0.26 g of the compound obtained in example 7 was dispersed in 30 ml of anhydrous glycol dimethyl ether under nitrogen, followed by dropwise addition of a 1M potassium tert-butoxide solution in tetrahydrofuran at room temperature. After the addition, the mixture was allowed to react for 30 min, and 0.29 g of 2-bromo-3-bromomethylquinoline was added thereto. The system was heated to reflux for 6 h, and then cooled to room temperature. 10 ml of water was added, and pH was adjusted to 2-3 with a 1N diluted hydrochloric acid. The obtained mixture was extracted with dichloromethane for 3-4 times, and the organic phase was combined, washed with water and saturated saline aqueous solution, dried over anhydrous sodium sulfate, and evaporated to obtain crude product, which was subjected to silica gel column chromatography (dichloromethane:methanol=60:1) to obtain 0.29 g of white solid. Yield: 63%.

$^1$HNMR (CDCl$_3$) (ppm): 0.75 (3H, t), 1.96 (1H, m), 2.09 (1H, m), 2.14 (3H, s), 2.78 (1H, s), 5.12 (1H, d), 5.30 (1H, d), 5.43 (1H, d), 5.92 (1H, d), 5.99 (1H, d), 6.53 (1H, d), 7.60 (2H, m), 7.75 (1H, m), 7.83 (1H, d), 8.17 (2H, t).

Preparation of (20S,20aR)-20a-acetoxyhomocamptothecin (Compound ysb-1)

The starting material 15 (50 mg), palladium acetate (5 mg), tri-(o-tolyl)phosphine (27 mg), potassium acetate (30 mg) and tetrabutylammonium Chloride (30 mg) were dispersed in 20 ml anhydrous acetonitrile under nitrogen, and heated to reflux for 15 h. Then, the mixture was cooled to room temperature, adjusted pH to 3-4 with a 1N diluted hydrochloric acid. After stirred for 30 min, the mixture was rotarily evaporated to dryness, and the residue was subjected to silica gel column chromatography (dichloromethane:methanol=60:1) to obtain 20 mg of yellowish solid. Yield: 50%.

$^1$HNMR (500 MHz, DMSO-D$_6$): 0.68 (t, J=7.5 Hz, 3H), 2.01 (m, 1H), 2.19 (m, 1H), 2.23 (s, 3H), 5.30 (s, 2H), 5.53 (d, J=15.2 Hz, 1H), 5.68 (d, J=15.4 Hz, 1H), 6.03 (s, 1H), 6.29 (s, 1H), 7.42 (s, 1H), 7.72 (m, 1H), 7.88 (m, 1H), 8.13 (d, J=8.2 Hz, 1H), 8.18 (d, J=8.5 Hz, 1H), 8.70 (s, 1H), ppm; $^{13}$C NMR (300 MHz, DMSO-D$_6$): 8.62, 20.43, 32.06, 50.53, 60.87, 70.49, 76.26, 99.11, 123.15, 127.62, 127.95, 128.48, 128.90, 129.82, 130.34, 131.51, 144.92, 147.87, 152.45, 153.12, 158.85, 167.75, 169.78, ppm; HRMS (ESI): m/z calcd for C$_{23}$H$_{21}$N$_2$O$_6$ [M+H]$^+$ 421.1394, found 421.1394.

EXAMPLE 9

Preparation of (20S,20aR)-20a-hydroxylhomocamptothecin (Compound ysb-2)

(20S,20aR)-20a-acetoxyhomocamptothecin (ysb-1, 0.11 g) was dispersed in 20 ml of methanol, and 0.1 g of sodium hydroxide was added thereto. The mixture was stirred for 3 h, and then 5 ml of trifluoroacetic acid was added. Thereafter, the reaction continued at room temperature for 5 h. The reaction mixture was filtered, and the filter cake was washed with methanol and water for twice, respectively, and baked to dryness to obtain 65 mg of white solid. Yield: 60%.

$^1$HNMR (500 MHz, DMSO-D$_6$): 0.71 (t, J=7.5 Hz, 3H), 1.85 (m, 1H), 2.30 (m, 1H), 5.25 (m, 4H), 5.39 (d, J=14.5 Hz, 1H), 5.68 (d, J=15.0 Hz, 1H), 5.82 (s, 1H), 7.42 (s, 1H), 7.72 (m, 1H), 7.87 (m, 1H), 8.13 (d, J=8.0 Hz, 1H), 8.18 (d, J=8.0 Hz, 1H), 8.69 (s, 1H), ppm; $^{13}$C NMR (300 MHz, DMSO-D$_6$): 8.65, 31.96, 50.42, 60.52, 68.75, 77.32, 99.66, 123.32, 127.55, 127.90, 128.46, 128.90, 129.81, 130.30, 131.47, 144.51, 147.87, 152.56, 153.93, 158.92, 173.15, ppm; HRMS (ESI): m/z calcd for C$_{21}$H$_{19}$N$_2$O$_5$[M+H]$^+$ 379.1288, found 379.1266.

EXAMPLE 10

Preparation of (20S,20aR)-10-methoxy-20a-acetoxyhomocamptothecin (Compound ysb-3)

The procedure was conducted in the same manner as example 8 to obtain compound ysb-3 as a yellowish solid, except using 2-bromo-3-bromomethyl-6-methoxyquinoline to replace 2-bromo-3-bromomethylquinoline as a starting material. Yield: 55%.

$^1$HNMR (500 MHz, DMSO-D$_6$): 0.68 (t, J=7.5 Hz, 3H), 2.01 (m, 1H), 2.19 (m, 1H), 2.23 (s, 3H), 3.95 (s, 3H), 5.30 (s, 2H), 5.53 (d, J=15.2 Hz, 1H), 5.68 (d, J=15.4 Hz, 1H), 6.03 (s, 1H), 6.29 (s, 1H), 7.42 (s, 1H), 7.88 (m, 1H), 8.13 (d, J=8.2 Hz, 1H), 8.18 (d, J=8.5 Hz, 1H), 8.70 (s, 1H), ppm; $^{13}$C NMR (300 MHz, DMSO-D$_6$): 8.61, 20.42, 32.07, 50.53, 55.54, 60.87, 70.49, 76.26, 79.12, 98.43, 106.26, 122.50, 122.98, 129.44, 129.98, 130.25, 130.36, 143.97, 145.18, 153.16, 158.16, 158.86, 167.76, 169.78, ppm; HRMS (ESI): m/z calcd for C$_{24}$H$_{23}$N$_2$O$_7$ [M+H]$^+$ 451.1500, found 451.1502.

EXAMPLE 11

Preparation of (20S,20aR)-10-methoxy-20a-hydroxylhomocamptothecin (Compound ysb-4)

The procedure was conducted in the same manner as example 9 to obtain compound ysb-4 as a yellowish solid, except using ysb-3 to replace ysb-1 as a starting material. Yield: 58%.

$^1$HNMR (500 MHz, DMSO-D$_6$): 0.72 (t, J=7.5 Hz, 3H), 1.88 (m, 1H), 2.30 (m, 1H), 3.95 (s, 3H), 5.26 (m, 4H), 5.39 (d, J=14.5 Hz, 1H), 5.68 (d, J=15.0 Hz, 1H), 5.82 (s, 1H), 7.42 (s, 1H), 7.87 (m, 1H), 8.13 (d, J=8.0 Hz, 1H), 8.18 (d, J=8.0 Hz, 1H), 8.69 (s, 1H), ppm; $^{13}$C NMR (300 MHz, DMSO-D$_6$): 8.29, 31.90, 50.10, 55.49, 60.43, 68.98, 76.99, 98.76, 106.24, 122.43, 122.53, 129.15, 129.65, 129.89, 130.15, 143.85, 144.54, 149.97, 153.72, 157.98, 158.73, 172.70, ppm; HRMS (ESI): m/z calcd for C$_{22}$H$_{20}$N$_2$NaO$_6$ [M+Na]$^+$ 431.1214, found 431.1286.

EXAMPLE 12

Preparation of (20S,20aR)-9,10-(1,3-dioxolane)-20a-acetoxyhomocamptothecin (Compound ysb-5)

The procedure was conducted in the same manner as example 8 to obtain compound ysb-5 as a yellowish solid, except using 2-bromo-3-bromomethyl-6,7-(1,3-dioxolane)-quinoline to replace 2-bromo-3-bromomethylquinoline as a starting material. Yield: 61%.

$^1$HNMR (500 MHz, DMSO-D$_6$): 0.68 (t, J=7.5 Hz, 3H), 1.99 (m, 1H), 2.17 (m, 1H), 2.22 (s, 3H), 5.22 (s, 2H), 5.50 (d, J=15.1 Hz, 1H), 5.68 (d, J=15.4 Hz, 1H), 6.01 (s, 1H), 6.26 (s, 1H), 6.28 (s, 2H), 7.30 (s, 1H), 7.51 (d, J=6.6 Hz, 1H), 8.46 (s, 1H), ppm; $^{13}$C NMR (300 MHz, DMSO-D$_6$): 8.61, 20.42, 32.07, 50.47, 60.88, 70.49, 76.42, 98.28, 101.53, 103.06, 104.68, 122.24, 125.60, 128.40, 130.10, 145.32, 146.50, 148.61, 149.81, 151.30, 153.15, 158.85, 167.77, 169.78, ppm; HRMS (ESI): m/z calcd for C$_{24}$H$_{21}$N$_2$O$_8$[M+H]$^+$ 465.1292, found 465.1280.

EXAMPLE 13

Preparation of (20S,20aR)-9,10-(1,3-dioxolane)-20a-hydroxylhomocamptothecin (Compound ysb-6)

The procedure was conducted in the same manner as example 9 to obtain compound ysb-6 as a yellowish solid, except using ysb-5 to replace ysb-1 as a starting material. Yield: 56%.

$^1$HNMR (500 MHz, DMSO-D$_6$): 0.70 (t, J=7.5 Hz, 3H), 1.83 (m, 1H), 2.30 (m, 1H), 5.23 (m, 4H), 5.36 (d, J=15.2 Hz, 1H), 5.58 (d, J=15.0 Hz, 1H), 5.78 (s, 1H), 6.28 (s, 2H), 7.30 (s, 1H), 7.50 (d, J=6.6 Hz, 2H), 8.46 (s, 1H), ppm; HRMS (ESI): m/z calcd for C$_{22}$H$_{18}$N$_2$NaO$_7$ [M+Na]$^+$ 445.1006, found 445.1017.

EXAMPLE 14

Preparation of (20S,20aR)-9,10-(1,4-dioxolane)-20a-acetoxyhomocamptothecin (Compound ysb-7)

The procedure was conducted in the same manner as example 8 to obtain compound ysb-7 as a yellowish solid, except using 2-bromo-3-bromomethyl-6,7-(1,4-dioxolane)-quinoline to replace 2-bromo-3-bromomethylquinoline as a starting material. Yield: 58%.

$^1$HNMR (500 MHz, DMSO-D$_6$): 0.68 (t, J=7.5 Hz, 3H), 1.99 (m, 1H), 2.18 (m, 1H), 2.22 (s, 3H), 4.43 (s, 4H), 5.21 (s, 2H), 5.50 (d, J=15.1 Hz, 1H), 5.68 (d, J=15.4 Hz, 1H), 6.01 (s, 1H), 6.25 (s, 1H), 7.32 (s, 1H), 7.54 (d, J=2.1 Hz, 2H), 8.45 (s, 1H), ppm; $^{13}$C NMR (300 MHz, DMSO-D$_6$): 8.75, 20.55, 32.20, 50.53, 54.94, 61.02, 64.35, 70.63, 76.40, 98.77, 112.16, 113.04, 122.61, 113.04, 122.61, 124.24, 128.03, 129.72, 144.50, 145.38, 147.61, 150.59, 153.34, 159.03, 168.00, 170.02, ppm; HRMS (ESI): m/z calcd for C$_{25}$H$_{23}$N$_2$O$_8$[M+H]$^+$ 479.1449, found 479.1469.

EXAMPLE 15

Preparation of (20S,20aR)-9,10-(1,4-dioxolane)-20a-hydroxyl homocamptothecin (Compound ysb-8)

The procedure was conducted in the same manner as example 9 to obtain compound ysb-8 as a yellowish solid, except using ysb-7 to replace ysb-1 as a starting material. Yield: 57%.

$^1$HNMR (500 MHz, DMSO-D$_6$): 0.70 (t, J=7.5 Hz, 3H), 1.83 (m, 1H), 2.30 (m, 1H), 4.43 (s, 4H), 5.24 (m, 4H), 5.37 (d, J=15.2 Hz, 1H), 5.58 (d, J=15.0 Hz, 1H), 5.79 (s, 1H), 7.32 (s, 1H), 7.50 (d, J=3.3 Hz, 2H), 8.45 (s, 1H), ppm; HRMS (ESI): m/z calcd for C$_{23}$H$_{21}$N$_2$O$_7$ [M+H]$^+$ 437.1343, found 437.1344.

EXAMPLE 16

Preparation of (20S,20aR)-10-hydroxyl-7-ethyl-20a-acetoxy homocamptothecin (Compound ysb-9)

The procedure was conducted in the same manner as example 8 to obtain compound ysb-9 as a yellowish solid, except using 2-bromo-3-bromomethyl-4-ethyl-6-hydroxyquinoline to replace 2-bromo-3-bromomethylquinoline as a starting material. Yield: 40%.

$^1$HNMR (500 MHz, DMSO-D$_6$): 0.68 (t, J=7.5 Hz, 3H), 1.30 (t, J=10.0 Hz, 3H), 1.88 (m, 2H), 2.22 (s, 3H), 3.09 (q, J=10.0 Hz, 2H), 5.21 (s, 2H), 5.50 (d, J=15.1 Hz, 1H), 5.68 (d, J=15.4 Hz, 1H), 6.01 (s, 1H), 6.25 (s, 1H), 7.32 (s, 1H), 7.43 (m, 1H), 7.54 (d, J=2.1 Hz, 2H), 8.45 (s, 1H), 10.3 (s, 1H), ppm.

EXAMPLE 17

Preparation of (20S,20aR)-10-hydroxyl-7-ethyl-20a-hydroxyl homocamptothecin (Compound ysb-10)

The procedure was conducted in the same manner as example 9 to obtain compound ysb-10 as a yellowish solid, except using ysb-9 to replace ysb-1 as a starting material. Yield: 56%.

$^1$HNMR (500 MHz, DMSO-D$_6$): 0.68 (t, J=7.5 Hz, 3H), 1.30 (t, J=10.0 Hz, 3H), 1.88 (m, 2H), 3.09 (q, J=10.0 Hz, 2H), 5.21 (s, 2H), 5.50 (d, J=15.1 Hz, 1H), 5.68 (d, J=15.4 Hz, 1H), 5.78 (s, 1H), 6.01 (s, 1H), 6.25 (s, 1H), 7.32 (s, 1H), 7.43 (m, 1H), 7.54 (d, J=2.1 Hz, 2H), 8.45 (s, 1H), 10.1 (s, 1H), ppm.

EXPERIMENTAL EXAMPLE 18

Anti-Tumor Activity Assay

All the cytotoxic activity assays of the compounds were conducted on corresponding tumor cell lines. There were 6000~10000 tumor cells per 100 μL of culture medium, and they were placed in a 96-well plate (Falcon, Calif.). The tumor cells were divided into 3 parts, and treated with drugs having gradient concentrations. The tumor cells were cultivated for 72 h at 37° C., and assayed using SRB method. The concentration that 50% of the growth of the tumor cells growth was inhibited, i.e., IC50, was calculated from dosage-activity curves.

TABLE 1

The growth inhibition activity on HCT-116 and A549 cells

| Compound No. | Formula | IC$_{50}$, nM | |
|---|---|---|---|
| | | HCT-116 | A549 |
| Ysb-1 | (structure) | 14.2 ± 6.1 | 49.2 ± 34.6 |
| Ysb-2 | (structure) | 49.3 ± 15.0 | 16.8 ± 4.2 |

TABLE 1-continued

The growth inhibition activity on HCT-116 and A549 cells

| Compound No. | Formula | IC$_{50}$, nM | |
|---|---|---|---|
| | | HCT-116 | A549 |
| Ysb-3 | | 4.4 ± 1.0 | 4.7 ± 1.1 |
| Ysb-4 | | 10.6 ± 6.2 | 4.8 ± 3.6 |
| Ysb-5 | | 2.1 ± 0.3 | 1.2 ± 0.7 |
| Ysb-6 | | 3.1 ± 0.7 | 3.1 ± 1.6 |
| Ysb-7 | | 4.9 ± 4.1 | 4.6 ± 2.9 |
| Ysb-8 | | 3.4 ± 1.2 | 2.9 ± 1.3 |

TABLE 1-continued

The growth inhibition activity on HCT-116 and A549 cells

| Compound No. | Formula | IC$_{50}$, nM | |
| --- | --- | --- | --- |
| | | HCT-116 | A549 |
| Ysb-9 | | 133.4 ± 18.7 | 225.7 ± 15.8 |
| Ysb-10 | | 366 ± 213 | 30.3 ± 18.4 |
| 10-HCPT | | 31.2 ± 8.2 | 33.6 ± 17.8 |
| SN-38 | | 40.8 ± 5.8 | 30.4 ± 11.5 |
| CPT | | 22.9 ± 12.0 | 33.8 ± 13.9 |

The above table demonstrated that the compounds of the present invention have very high growth inhibition against HCT-116 and A549 tumor cells, exhibiting an excellent antitumor activity.

The invention claimed is:

1. A camptothecin compound with stable 7-membered lactone ring represented by formula I, and pharmaceutically acceptable salts thereof,

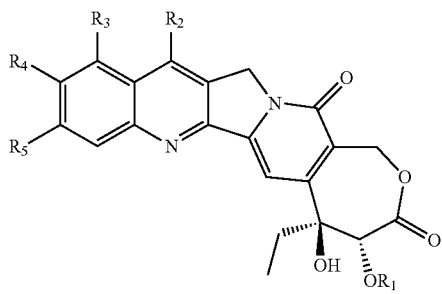

I wherein, $R_1$ is acetyl or propionyl;

$R_2$ is H, C1~C6 alkyl, C3~C6 cycloalkyl, piperidyl or C1~C6 alkyl substituted by amino;

$R_3$ is H, C1~C3 alkyl, or C1~C6 alkyl substituted by amino;

$R_4$ is H, hydroxyl, or C1~C6 alkoxyl;

$R_5$ is H, or C1~C6 alkoxyl;

or, $R_4$ and $R_5$ are linked to each other to form —OCH$_2$O— or —OCH$_2$CH$_2$O—.

2. The camptothecin compound with stable 7-membered lactone ring and pharmaceutically acceptable salts thereof according to claim 1, wherein $R_1$ is acetyl;

$R_2$ is H or C1~C3 alkyl;

$R_3$ is H or C1~C3 alkyl;

$R_4$ is H, hydroxyl, or C1~C6 alkoxyl;

$R_5$ is H, hydroxyl, or C1~C6 alkoxyl;

or, $R_4$ and $R_5$ are linked to each other to form —OCH$_2$O— or —OCH$_2$CH$_2$O—.

3. The camptothecin compound with stable 7-membered lactone ring and pharmaceutically acceptable salts thereof according to claim 1, $R_1$ is acetyl;

$R_2$ is H or ethyl;

$R_3$ is H or C1~C3 alkyl;

$R_4$ is H, hydroxyl, or methoxy;

$R_5$ is H;

or, $R_4$ and $R_5$ are linked to each other to form —OCH$_2$O— or —OCH$_2$CH$_2$O—.

4. The camptothecin compound with stable 7-membered lactone ring and pharmaceutically acceptable salts thereof according to claim 1, wherein, the camptothecin compound with stable 7-membered lactone ring and pharmaceutically acceptable salts thereof are as follows:

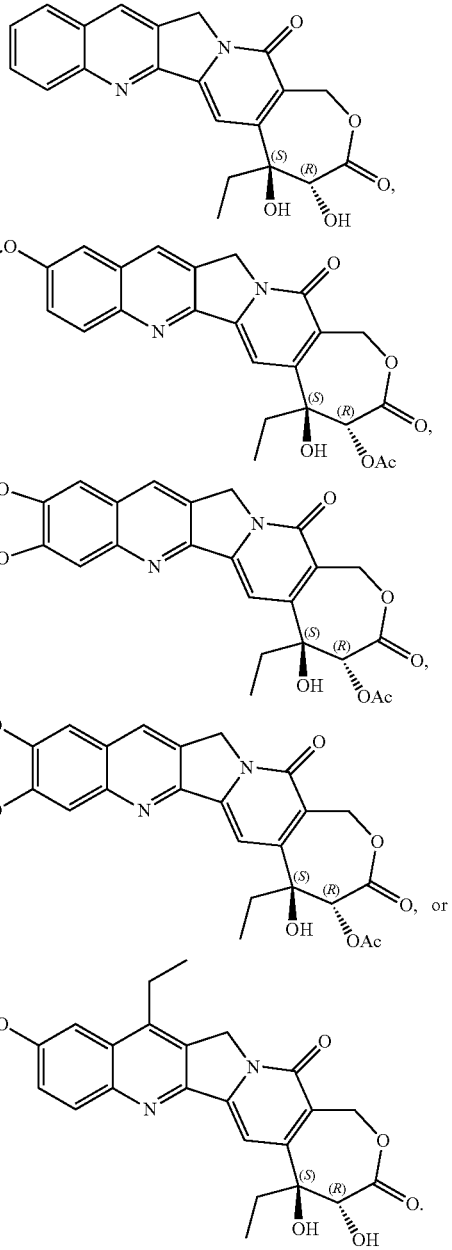

5. A method of preparing the camptothecin compound with 7-membered lactone ring, and pharmaceutically acceptable salts thereof according to claim 1, comprising the steps of:

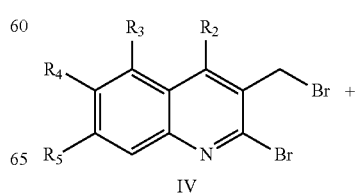

IV

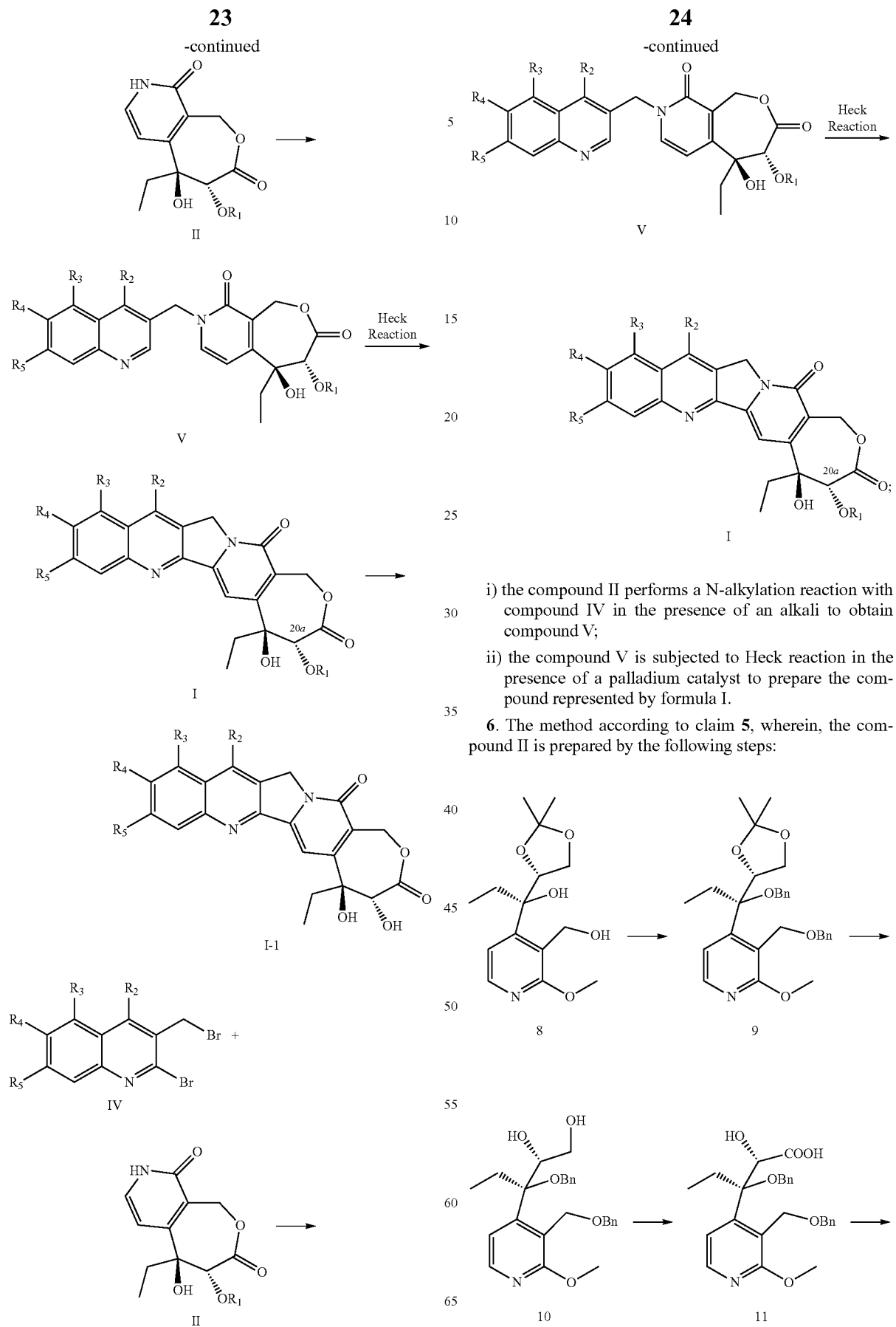
i) the compound II performs a N-alkylation reaction with compound IV in the presence of an alkali to obtain compound V;
ii) the compound V is subjected to Heck reaction in the presence of a palladium catalyst to prepare the compound represented by formula I.
6. The method according to claim 5, wherein, the compound II is prepared by the following steps:

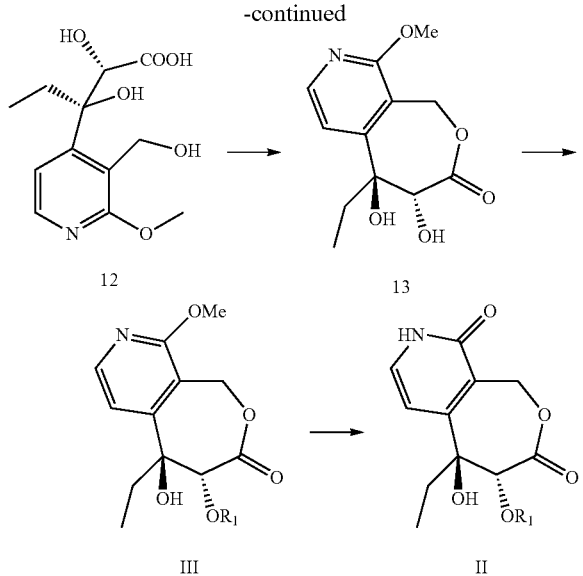

1) the compound 8 performs an etherification with benzyl bromide or benzyl chloride in the presence of an alkali to form compound 9;

2) the compound 9 is hydrolyzed in the presence of an acid to form compound 10;
3) the compound 10 is oxidized in the presence of an oxidant to produce compound 11;
4) the compound 11 is deprotected by removing the protection group of benzyl in the presence of a catalytic hydrogenation system to obtain compound 12;
5) the compound 12 is converted into compound 13 containing a lactone ring in the presence of an acid;
6) the compound 13 is acylated by an anhydride or acyl chloride corresponding to the product in the presence of an alkali to form compound III;
7) the compound III is demethylated in the presence of iodotrimethylsilane, boron tribromide, or silicon tetrachloride to obtain a 2-pyridinone compound II as a key intermediate.

7. A composition for treating a colon or lung cancer, comprising a therapeutically effective amount of one or more selected from the group consisting of the camptothecin compound and pharmaceutically acceptable salts thereof according to claim 1, and pharmaceutically acceptable carriers.

8. A method for treating colon or lung cancer comprising administration of the camptothecin compound and pharmaceutically acceptable salts thereof according to claim 1 to the subject needed to be treated.

* * * * *